United States Patent
Belfance et al.

(10) Patent No.: US 11,352,177 B2
(45) Date of Patent: Jun. 7, 2022

(54) VIAL WITH LID ATTACHMENT MECHANISM

(71) Applicant: CSP Technologies, Inc., Auburn, AL (US)

(72) Inventors: John Belfance, Phenix City, AL (US); Ronald Supranowicz, Jupiter, FL (US)

(73) Assignee: CSP TECHNOLOGIES, INC., Auburn, AL (US)

( * ) Notice: Subject to any disclaimer, the term of this patent is extended or adjusted under 35 U.S.C. 154(b) by 829 days.

(21) Appl. No.: 15/337,652

(22) Filed: Oct. 28, 2016

(65) Prior Publication Data
US 2017/0043914 A1    Feb. 16, 2017

Related U.S. Application Data

(62) Division of application No. 13/884,053, filed as application No. PCT/US2011/063017 on Dec. 2, 2011, now abandoned.
(Continued)

(51) Int. Cl.
*B65D 43/22* (2006.01)
*B65D 43/16* (2006.01)
(Continued)

(52) U.S. Cl.
CPC ............... *B65D 43/22* (2013.01); *A61J 1/03* (2013.01); *B29D 22/003* (2013.01);
(Continued)

(58) Field of Classification Search
CPC .... B65D 43/162; B65D 43/22; B65D 81/266; B65D 51/30; B65D 2543/00842;
(Continued)

(56) References Cited

U.S. PATENT DOCUMENTS 2,814,404 A * 11/1957 Towns ................... B65D 41/28
                                                    215/320
2,894,654 A     7/1959 Lohrer
(Continued)

FOREIGN PATENT DOCUMENTS

DE          20111801 U1      9/2001

OTHER PUBLICATIONS

International Search Report issued in corresponding application PCT/US11/63017, dated Apr. 3, 2012.
(Continued)

*Primary Examiner* — Anthony D Stashick
*Assistant Examiner* — Blaine G Neway
(74) *Attorney, Agent, or Firm* — David B. Gornish; Eckert Seamans Cherin & Mellott, LLC

(57) ABSTRACT

A re-sealable container is disclosed having a lid, a body, an attachment mechanism, and a seal. The seal may extend from, or be attached to, the lid and engage at least a portion of the body, such as the side wall, including the body sealing surface and/or the lip. The engagement of the seal and body creates a seal that prevents the ingress of moisture and ambient conditions into an interior space of the body. The attachment mechanism may retain the lid in a seated, closed position on the body. The configuration of the seal and attachment mechanism accommodate a degree of error in the joining and placement of the lid and body while allowing for both the formation of a seal between the lid and body and the locking of the lid when the lid is in a closed position.

18 Claims, 14 Drawing Sheets

Related U.S. Application Data

(60) Provisional application No. 61/422,287, filed on Dec. 13, 2010.

(51) Int. Cl.
   - G01N 33/487 (2006.01)
   - B65D 81/26 (2006.01)
   - B65D 53/04 (2006.01)
   - B29D 22/00 (2006.01)
   - A61J 1/03 (2006.01)

(52) U.S. Cl.
   CPC .......... B65D 43/162 (2013.01); B65D 53/04 (2013.01); B65D 81/266 (2013.01); G01N 33/4875 (2013.01); *B65D 2251/01* (2013.01); *B65D 2251/1016* (2013.01); *B65D 2251/1058* (2013.01); *B65D 2251/1066* (2013.01); *B65D 2251/20* (2013.01); *B65D 2543/00833* (2013.01)

(58) Field of Classification Search
   CPC ... B65D 2543/00833; G01N 33/48778; G01N 33/4875; A61J 1/03
   See application file for complete search history.

(56) References Cited

U.S. PATENT DOCUMENTS

| | | | | |
|---|---|---|---|---|
| 3,240,405 | A * | 3/1966 | Abbott | B65D 47/0838 222/543 |
| 4,236,653 | A * | 12/1980 | Gach | B65D 47/0838 222/153.14 |
| 4,393,976 | A * | 7/1983 | Maguire | B65D 50/067 215/211 |
| 4,713,219 | A | 12/1987 | Gerken et al. | |
| 4,834,234 | A * | 5/1989 | Sacherer | B65D 39/0023 206/204 |
| 4,874,102 | A * | 10/1989 | Jessop | B01L 3/50825 215/273 |
| 4,917,131 | A * | 4/1990 | Contreras, Sr. | A45D 40/22 132/286 |
| 5,083,671 | A | 1/1992 | Hayes | |
| 5,253,551 | A * | 10/1993 | DeVaughn | B01L 3/5021 422/918 |
| 5,575,399 | A * | 11/1996 | Intini | B65D 21/0233 220/835 |
| 5,667,094 | A | 9/1997 | Rapchak et al. | |
| 5,788,064 | A | 8/1998 | Sacherer et al. | |
| 6,851,586 | B2 | 2/2005 | Odet | |
| 7,665,601 | B2 | 2/2010 | Portier | |
| 8,006,368 | B2 | 8/2011 | Logel et al. | |
| 8,123,065 | B2 * | 2/2012 | Mitsuhashi | B01L 3/50825 220/285 |
| 2006/0219727 | A1 | 10/2006 | Giraud | |
| 2007/0080093 | A1 | 4/2007 | Boozer et al. | |
| 2008/0185301 | A1* | 8/2008 | Merical | B29C 49/0005 206/204 |
| 2010/0051636 | A1 | 3/2010 | Logel et al. | |

OTHER PUBLICATIONS

Written Opinion issued in corresponding application PCT/US11/63017, dated Apr. 3, 2012.

International Preliminary Report on Patentability issued in corresponding application PCT/US11/63017, dated Mar. 18, 2013.

* cited by examiner

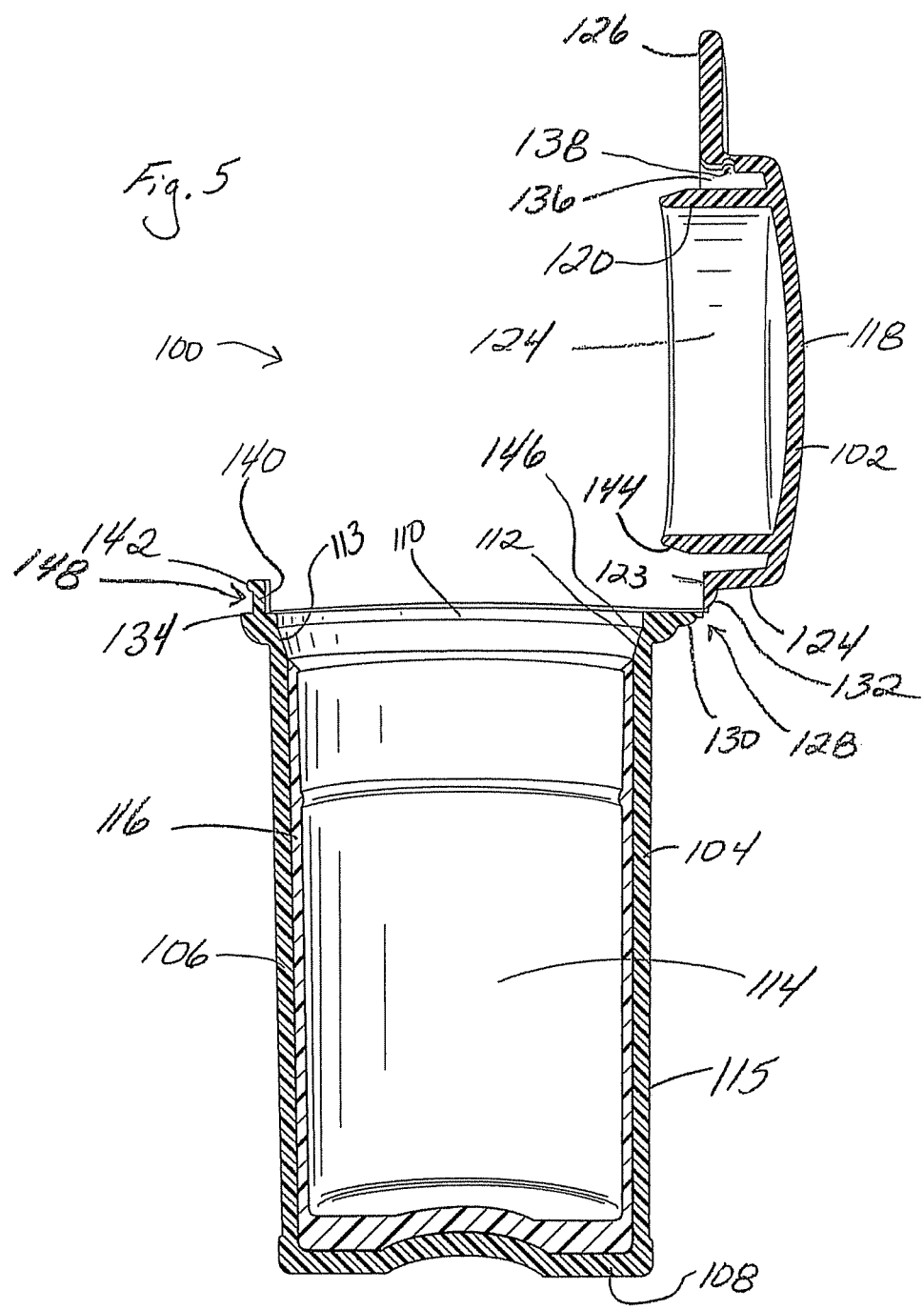

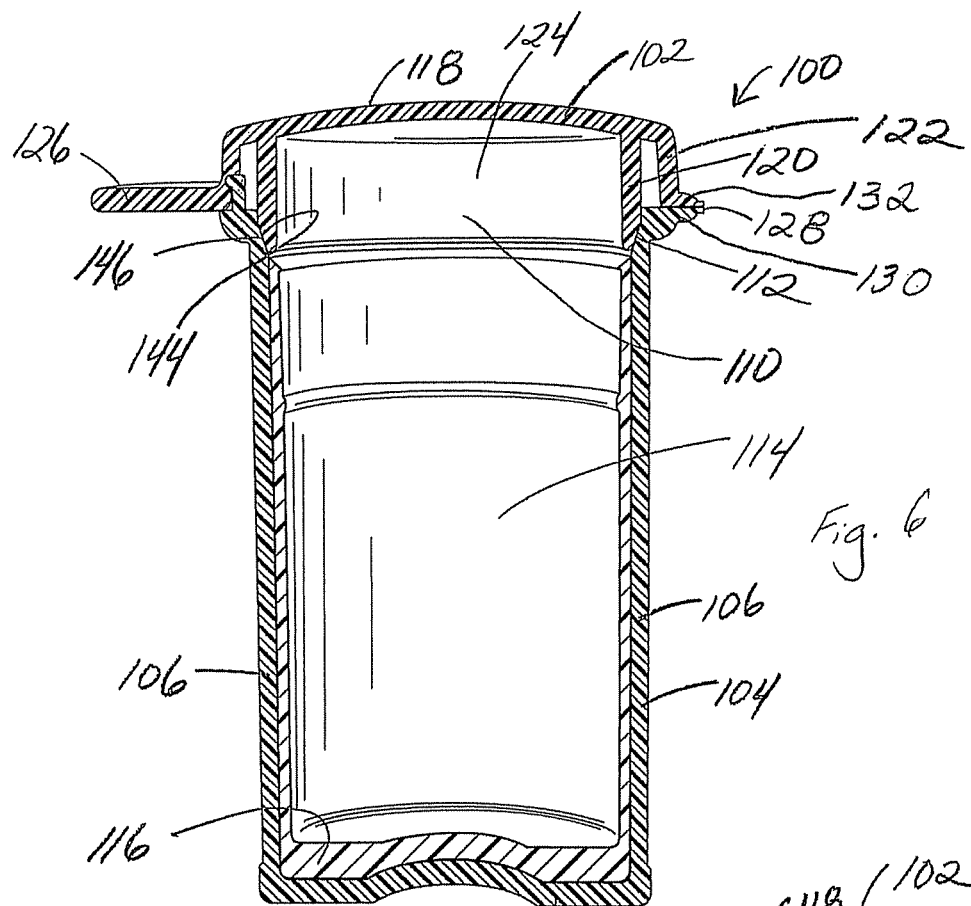
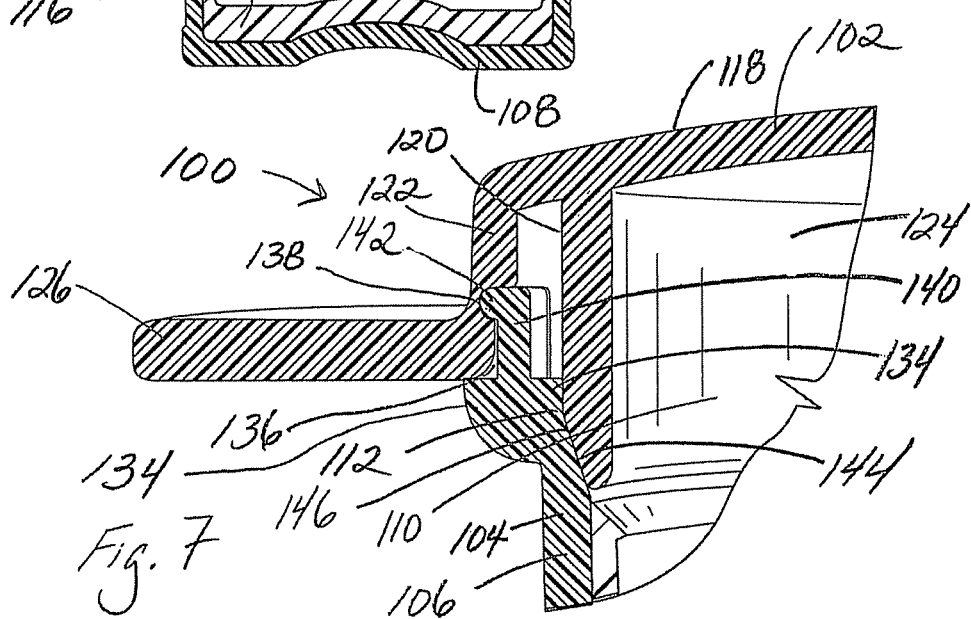

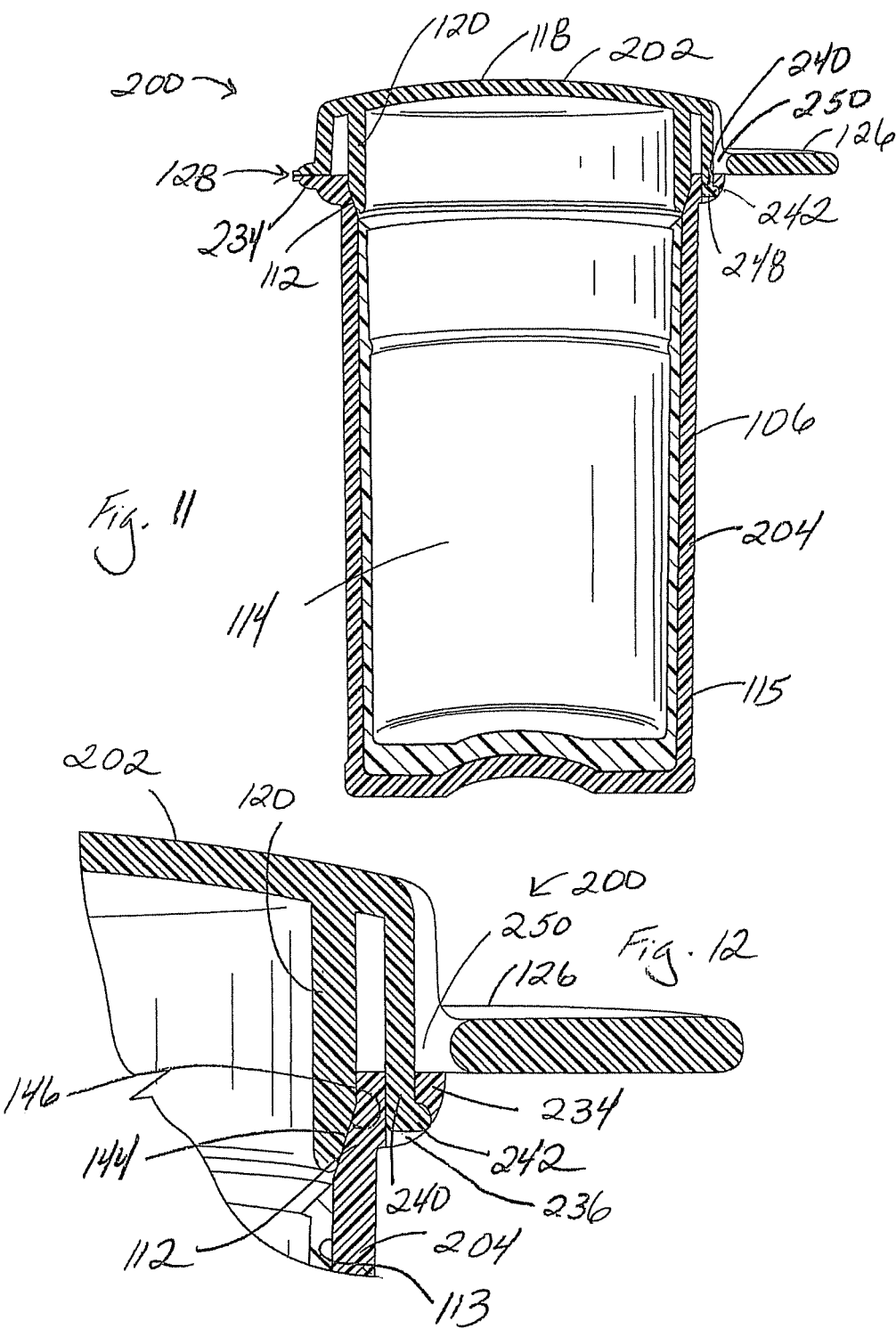

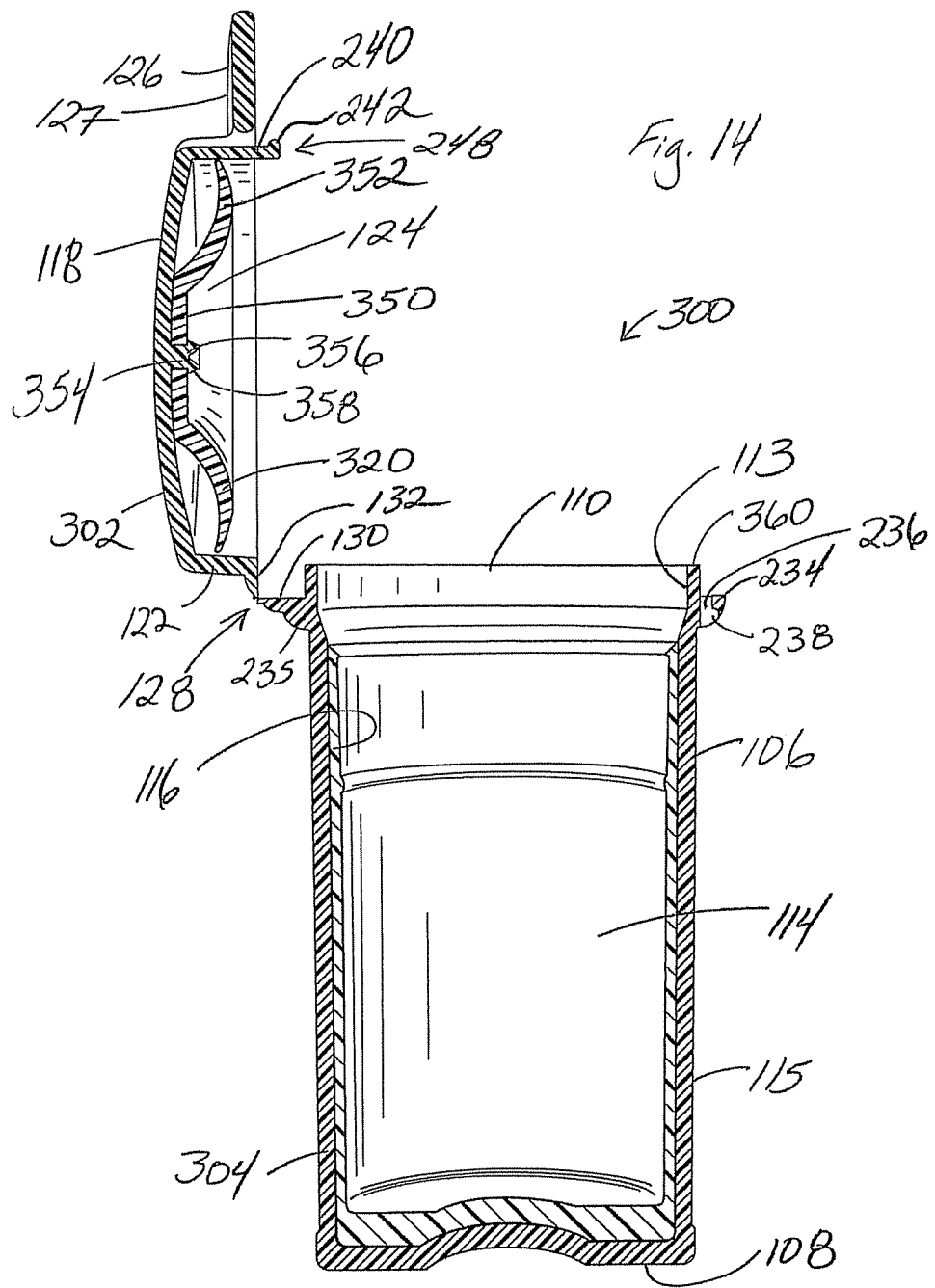

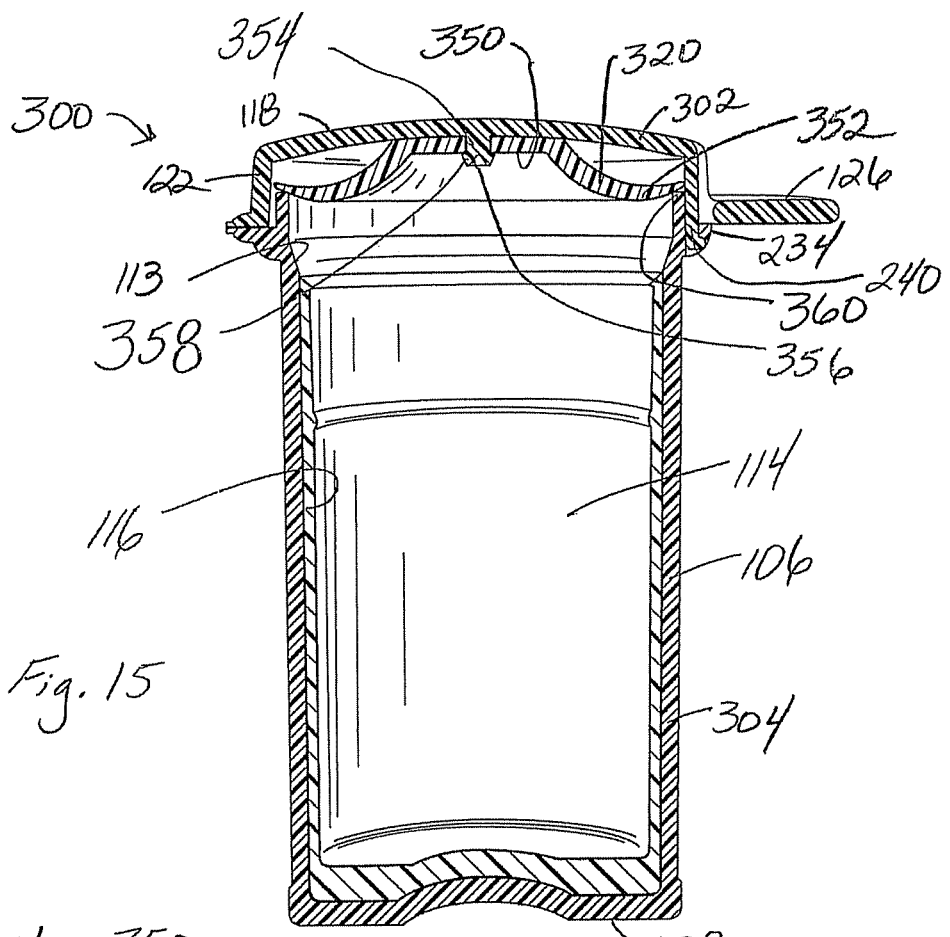
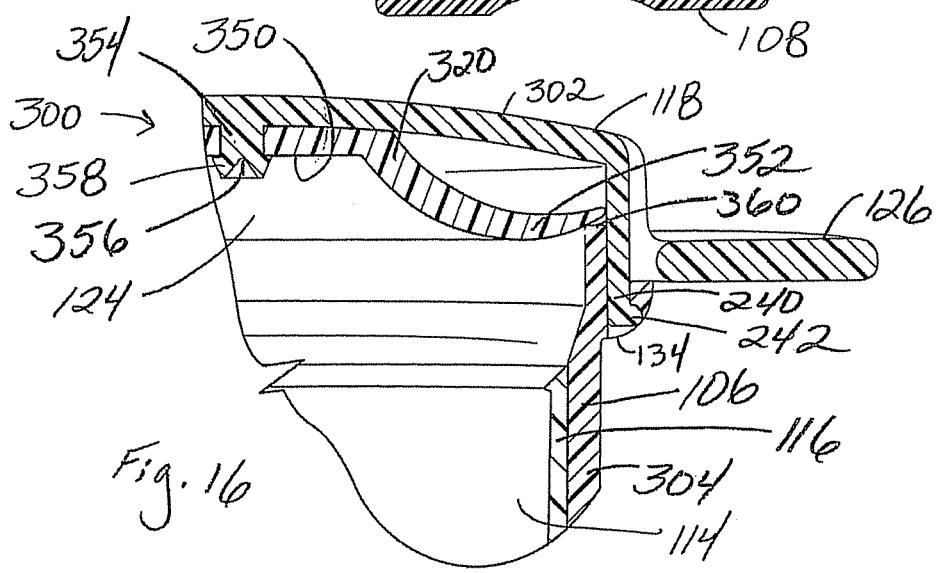

VIAL WITH LID ATTACHMENT MECHANISM

BACKGROUND

The present invention relates to containers that can be used to house glucose test strips, tablets, pills, solid dose pharmaceutical products, or other objects or moisture sensitive materials. More specifically, the present invention relates to resealable containers, such as, for example, vials, having a closeable lid, a body, and seal that controls the ingress and/or egress of moisture into/out of an interior space of the container, and which may be used to control the conditions in the interior space.

A container, such as a vial for example, typically includes a cap that is attached to a portion of the vial. With such devices, when the container is closed, the cap comes into contact with an upper lip of the vial, and through such contact may form a seal. However, because the upper lip of the vial of the container often has a relatively thin wall thickness, a degree of precision is typically required with respect to the positioning and connection between the cap and the vial to ensure a proper fit between the cap and upper lip of the vial so that the container properly closes.

To overcome issues relating to the limited permissible degree of error in the alignment and positioning of the cap relative to the vial, such containers are typically molded as a single, integral unit. Such an integral construction allows for the cap to remain attached to the vial when the container is open. Further, such an integral construction may alleviate potential problems with the container not properly closing due to an improper fit or misalignment between the attached cap and the vial, as integrally molding the components together may control the positioning and alignment of the cap relative to the vial. However, integrally molding both the cap and vial is typically more expensive than if the parts were molded separately.

SUMMARY

An aspect of the invention is a resealable container. The container includes a body having a sidewall, a base, and an opening. The base and the opening are disposed at opposite ends of the body. The sidewall is configured to provide an interior space in the body. Further, the interior space may be generally disposed between the opening and the base. Additionally, at least a portion of an inner surface of the sidewall may be a body sealing surface.

The lid includes a cap and a seal. The lid may be pivotably joined to the body to allow the lid to be moved between an open position and a closed position. Further, the lid may be configured to be seated on the body when the lid is in a closed position. When in an open position, the lid may allow access to the interior space. The seal may be configured to extend into at least a portion of the interior space of the body and engage at least a portion of the body sealing surface when the lid is in a closed position to form a seal between the body sealing surface and the seal.

The container also includes an attachment mechanism configured to secure the lid in a closed position and retain the seal between the body sealing surface and seal when the lid is seated on the body.

Another aspect of the invention is a resealable container that includes a body having a sidewall, a base, and an opening. The base and the opening may be disposed at opposite ends of the body. The sidewall may be configured to provide an interior space in the body. The interior space may be generally disposed between the opening and the base.

The lid may be pivotably joined to the body to allow the lid to be moved between an open position and a closed position. The lid may also be configured to be seated on the body when the lid is in a closed position and allow access to the opening when the lid is in an open position.

The container also includes a seal that is connected to the lid. The seal may have a sealing surface that engages a portion of the body adjacent to the interior space when the lid is in a closed position to form a seal between the body and the lid.

The container may also include an attachment mechanism configured to secure the lid in a closed position and retain the seal between the body and the lid when the lid is seated on the body.

Another aspect of the invention is a method of producing a resealable container. The method includes producing a body having a sidewall, a base, and an opening. The base and the opening may be disposed at opposite ends of the body. The sidewall may be configured to provide an interior space in the body. The interior space is generally disposed between the opening and the base. Further, at least a portion of an inner surface of the sidewall may have a body sealing surface.

The invention also includes producing a lid having a seal and attaching the lid to the body. The lid may be attached to the body to allow the lid to be pivotably moved between an open position and a closed position. Additionally, the lid may be configured to be seated on the body when the lid is in a closed position and allow access to the interior space when the lid is in an open position. The seal may be configured to extend into a least a portion of the interior space of the body and engage at least a portion of the body sealing surface when the lid is in a closed position to form a seal between the body sealing surface and the seal.

Additionally, at least one of the body or the lid includes an attachment mechanism configured to secure the lid in a closed position and retain the seal between the body sealing surface and seal when the lid is seated on the body.

Another aspect of the present invention is a method of producing a resealable container. The method includes producing a body having a sidewall, a base, and an opening. The base and the opening may be disposed at opposite ends of the body. The sidewall may be configured to provide an interior space in the body. The interior space may be generally disposed between the opening and the base. The method also includes producing a lid and connecting a seal to the lid. The seal may have sealing surface.

The method also includes attaching the lid to the body to allow the lid to be pivotably moved between an open position and a closed position. The lid may be configured to be seated on the body when the lid is in a closed position and allow access to the interior space when the lid is in an open position. The sealing surface may be configured to engage a portion of the body adjacent to the opening when the lid is in a closed position to form a seal between the body and the lid. Additionally, at least one of the body or lid includes an attachment mechanism configured to secure the lid in a closed position and retain the seal between the body and the lid when the lid is seated on the body.

The configuration of the seals and attachment mechanisms of the present invention accommodate a degree of error in the joining and placement of separate, or individual, lid and body components of the container, while still providing for both the formation of a seal between the lid and body and the locking of the lid in a closed position.

According to another exemplary embodiment, the attachment mechanism may include a claw having a protrusion.

According to another exemplary embodiment of the invention, the container includes a desiccant material.

According to another exemplary embodiment of the invention, the desiccant material is attached or adhered to an inner surface of the sidewall.

According to another exemplary embodiment, the sidewall includes a desiccant material.

According to another exemplary embodiment, the claw of the attachment mechanism is part of or connected to the body. According to such an embodiment, when the lid is in the closed position, the protrusion engages the lid to retain together the lid and the body. Further, the lid may include an aperture that houses at least a portion of the claw when the lid is in a closed position. The aperture may include a recess configured for the placement of the protrusion to facilitate the engagement of the protrusion with the lid to secure the lid to the body.

According to another exemplary embodiment, the claw of the attachment mechanism is part of or connected to the lid. According to such an embodiment, when the lid is in the closed position, the protrusion engages the body to retain together the lid and the body. Further, the body may include an aperture that houses at least a portion of the claw when the lid is in a closed position. The aperture may include a recess configured for the placement of the protrusion to facilitate the engagement of the protrusion with the body to secure the lid to the body.

BRIEF DESCRIPTION OF THE DRAWINGS

FIG. 5 is a cross sectional view of the container illustrated in FIG. 2 with the lid in the opened position.

FIG. 6 is a cross sectional view of the container illustrated in FIG. 2 with the lid in a closed position.

FIG. 7 is a cross sectional view of a portion of the container illustrated in FIG. 2 with the lid in a closed position.

FIG. 11 is a cross sectional view of the container illustrated in FIG. 9 with the lid in a closed position.

FIG. 12 is a cross sectional view of a portion of the container illustrated in FIG. 9 with the lid in a closed position.

FIG. 14 is a cross sectional view of the container illustrated in FIG. 13 with the lid in an opened position.

FIG. 15 is a cross sectional view of the container illustrated in FIG. 13 with the lid in a closed position.

FIG. 16 is a cross sectional view of a portion of the container illustrated in FIG. 13 with the lid in a closed position.

Figure 1:
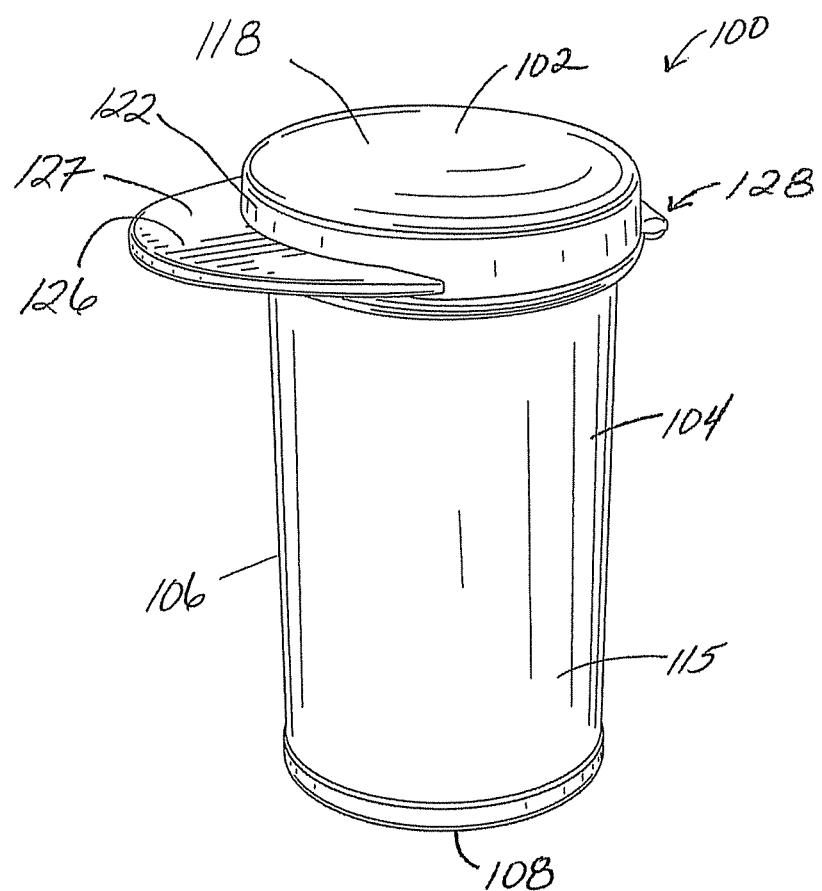
FIG. 1 is a perspective view of a container shown with the lid in a closed position.

The foregoing summary, as well as the following detailed description of certain embodiments, will be better understood when read in conjunction with the appended drawings. For the purpose of illustrating the invention, there is shown in the drawings, certain embodiments. It should be understood, however, that the present invention is not limited to the arrangements and instrumentalities shown in the attached drawings.

The following reference characters are used in the specification and figures:

| | |
|---|---|
| 100 | Container |
| 102 | Lid |
| 104 | Body |
| 106 | Sidewall |
| 108 | Base |
| 110 | Opening |
| 112 | Body sealing surface |
| 113 | Inner surface |
| 114 | Interior space |
| 115 | Outer surface |
| 116 | Desiccant material |
| 118 | Cap |
| 120 | Seal |
| 122 | Skirt |
| 123 | Seating surface |
| 124 | Upper interior region |
| 126 | Tab |
| 127 | Upper surface |
| 128 | Hinge |
| 130 | First extension |
| 132 | Second extension |
| 134 | Rim |
| 136 | Aperture |
| 138 | Recess |
| 140 | Claw |
| 142 | Protrusion |
| 144 | Tapered surface |
| 146 | Chamfered surface |
| 148 | Attachment mechanism |
| 200 | Container |
| 202 | Lid |
| 204 | Body |
| 234 | Rim |
| 235 | Lower surface |
| 236 | Aperture |
| 238 | Recess |
| 240 | Claw |
| 242 | Protrusion |
| 248 | Attachment mechanism |
| 250 | Orifice |
| 300 | Container |
| 302 | Lid |
| 304 | Body |
| 320 | Seal |
| 350 | Seal base |
| 352 | Sealing surface |
| 354 | Orifice |
| 356 | Pin |
| 358 | Shoulder |
| 360 | Lip |
| 400 | Container |
| 420 | Seal |
| 462 | First sealing surface |
| 464 | Second sealing surface |
| 466 | Sealing region |

DETAILED DESCRIPTION OF EXEMPLARY EMBODIMENTS

The present invention will now be described more fully with reference to the accompanying drawings, in which several embodiments are shown. This invention may, however, be embodied in many different forms and should not be construed as limited to the embodiments set forth here. Rather, these certain embodiments are examples of the invention, which has the full scope indicated by the language of the claims. Like numbers refer to like elements throughout.

Figure 2:
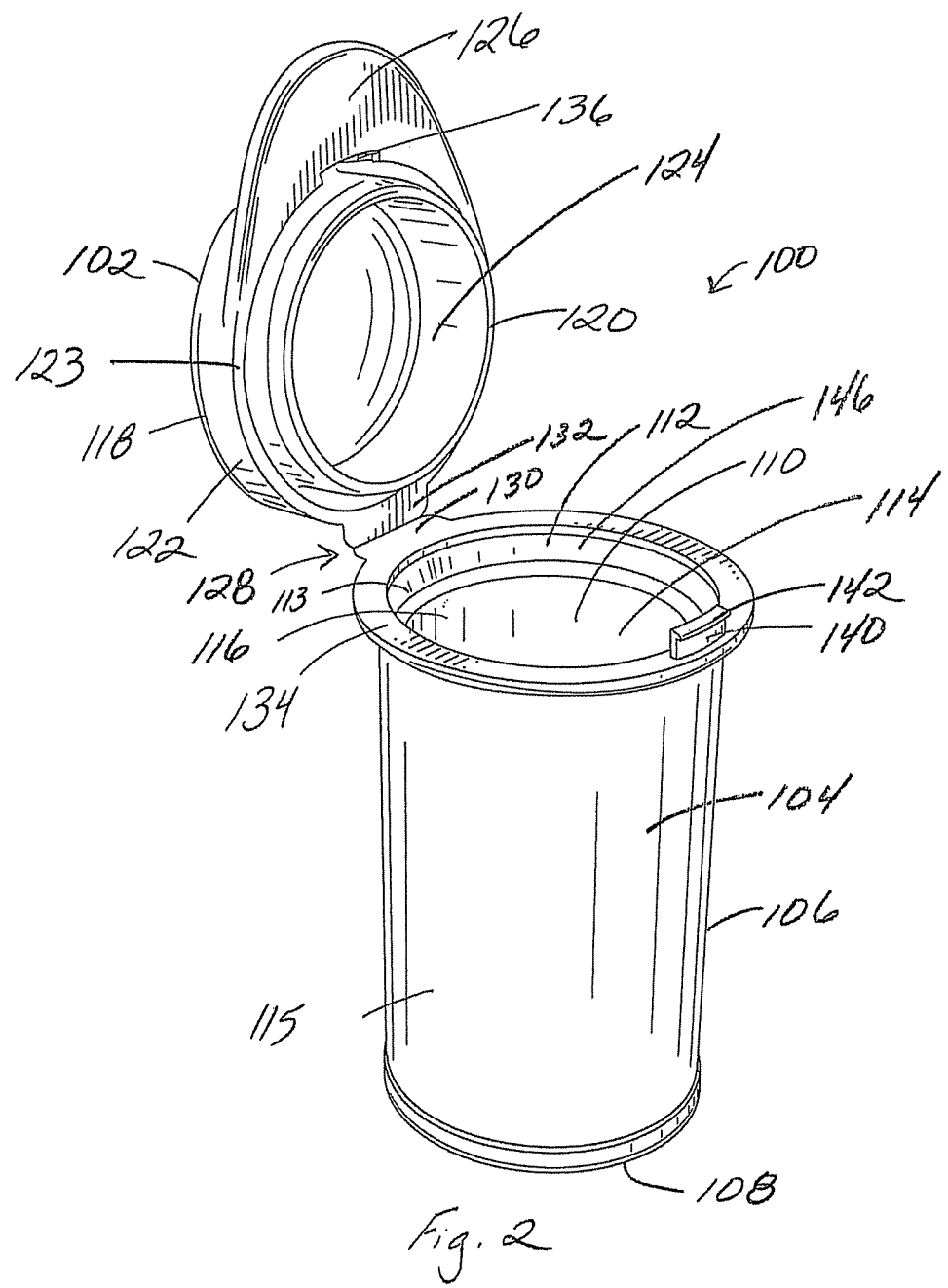
FIG. 2 is a perspective view of an embodiment of a container, shown with a lid in an opened position.

FIGS. 1 and 2 are perspective views of an embodiment of a container 100, shown with the lid 102 in closed and open positions, respectively. The container 100 may include a lid 102 and a body 104. The body 104 has a sidewall 106, a base 108, and an opening 110. At least a portion of the sidewall 106 adjacent to the opening 110 includes a body sealing surface 112. The base 108 and opening 110 may be positioned at opposing ends of the body 104.

The sidewall 106 may include an inner surface 113 and an outer surface 115. At least a portion of the inner surface 113 of the sidewall 106 may form or define at least a portion of an interior space 114 in the body 104 that may receive the insertion of an item(s) or product(s). The interior space 114 may be at least partially disposed between the base 108 and the opening 110. The opening 110 provides access to the interior space 114. According to an embodiment of the present invention, the opening 110 may be bound by a rim 134 that extends around at least a portion of the periphery of the opening 110. According to such an embodiment, when the lid 102 is in a closed position, at least a portion of the lid 102 may be seated upon at least a portion of the rim 134.

The body 104 may also include or house a desiccant material 116. For example, as shown in FIG. 2, the desiccant material 116 may be disposed within the interior space 114, such as, for example, being a liner or sleeve that may be positioned adjacent to and/or attached or adhered to the sidewall 106 and/or base 108. According to an embodiment, the desiccant material 106 may generally follow the shape of at least a portion of the inner surface 113 of the sidewall 106. Further, the desiccant material 116 may at least partially define the interior space 114. Alternatively, at least a portion of the body 106, such as, for example, the sidewall 106 and/or base 108, may be made from a desiccant material or a material containing a desiccant material. Further, the desiccant material 116 may be provided in the interior space 114 in the form of one or more sachets, canisters, or pellets, or in other particulate forms.

Suitable desiccant material 116 include injection-moldable thermoplastic desiccant polymeric material described in one or more of U.S. Pat. Nos. 5,911,937; 6,214,255; 6,130,263; 6,080,350; 6,174,952; 6,124,006; and 6,221,446, all to Hekal, and which are incorporated herein by reference. Silica gel, a molecular sieve, calcium oxides, or clay may also or instead be used directly as desiccants or incorporated into a desiccant material. In alternative embodiments, different types of absorbing materials, or alternatively, releasing materials, may be employed, including, for example, a material that can release a gas, such as an inert gas that prevents oxidation of an enclosed product, item, or medicament. Further, the releasing material may release a flavoring or fragrance, or moisture, in case of a product, item, or medicament housed in the interior space 114 should not be allowed to dry out.

Figure 3:
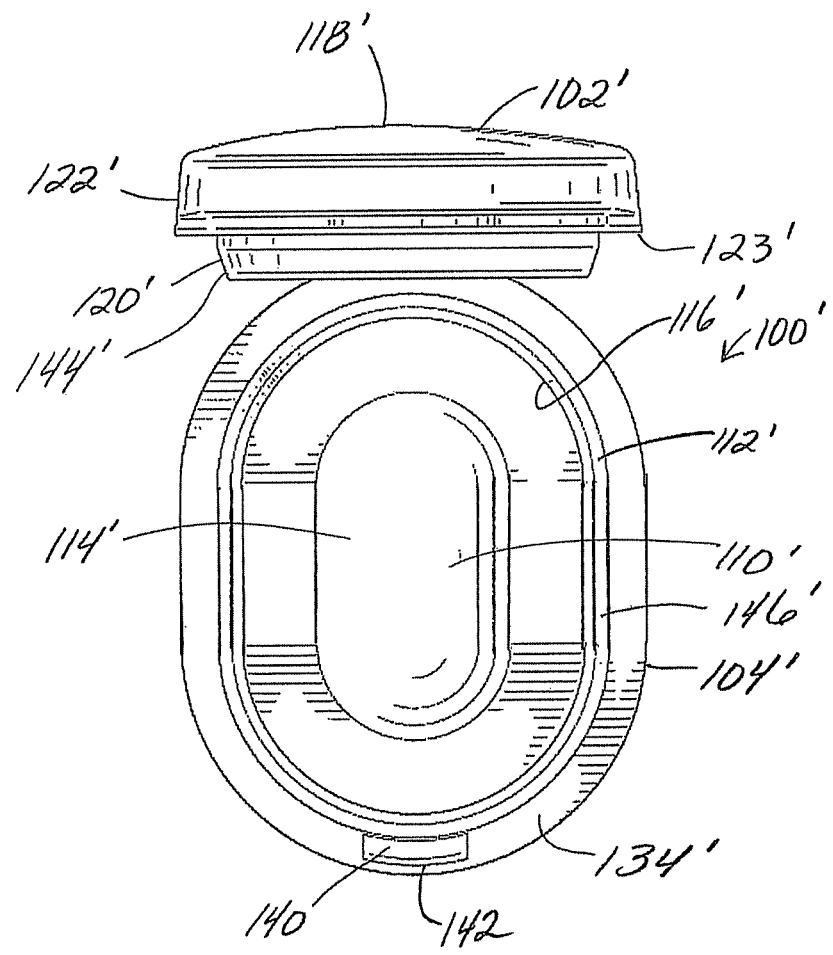
FIG. 3 is a top plan view of an embodiment of a container having a non-round configuration and with the lid in an open position.
Figure 4:
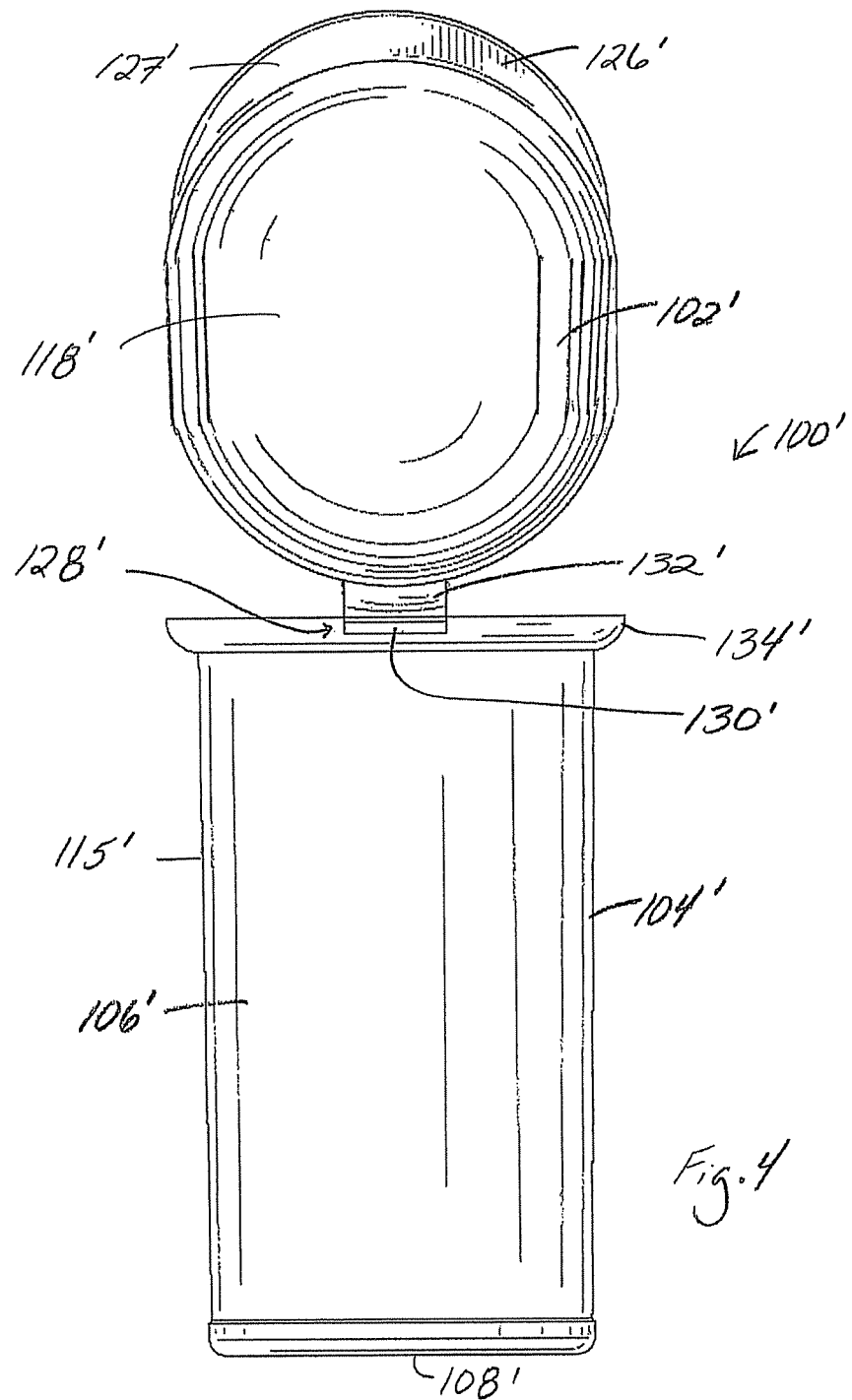
FIG. 4 is a rear view of an embodiment of a container having a non-round configuration and with the lid in an open position.
Figure 8:
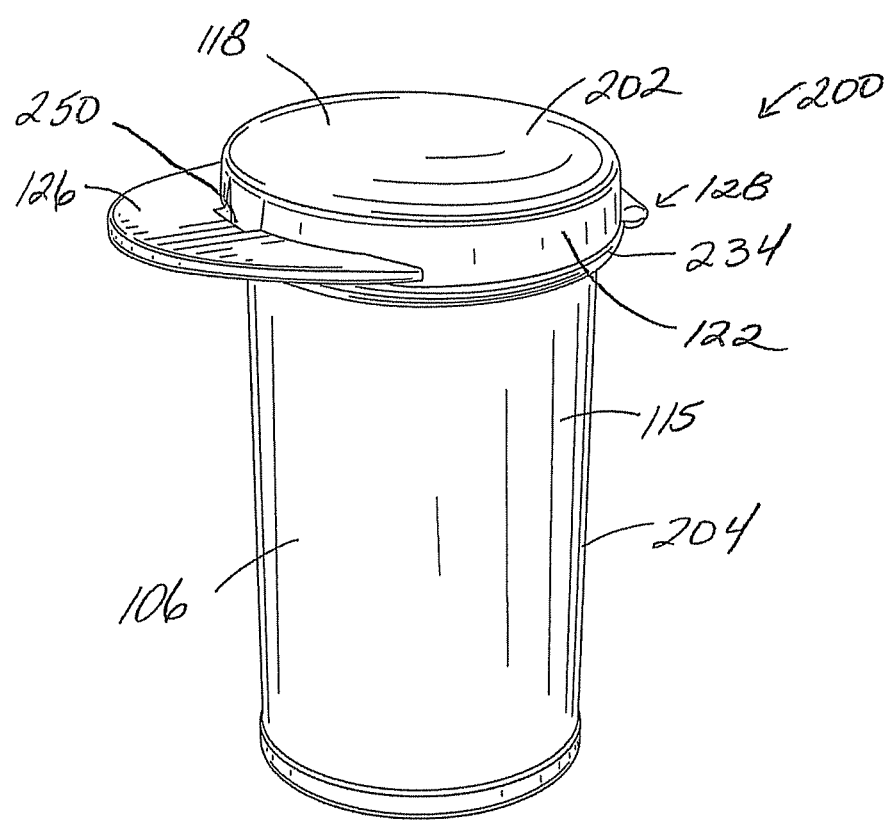
FIG. 8 is a perspective view of a container shown with the lid in a closed position.
Figure 9:
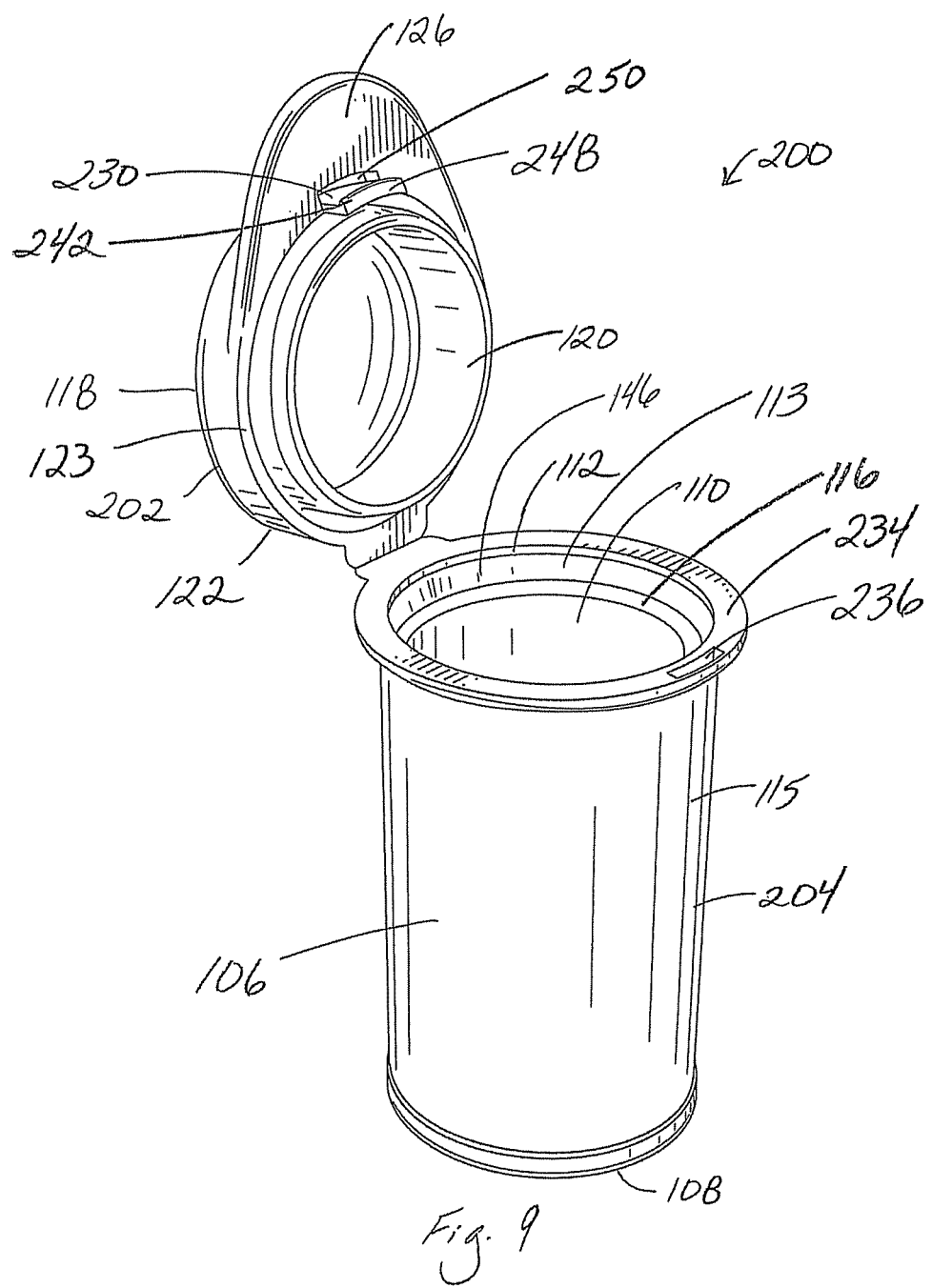
FIG. 9 is a perspective view of the container illustrated in FIG. 8, shown with a lid in an opened position.
Figure 10:
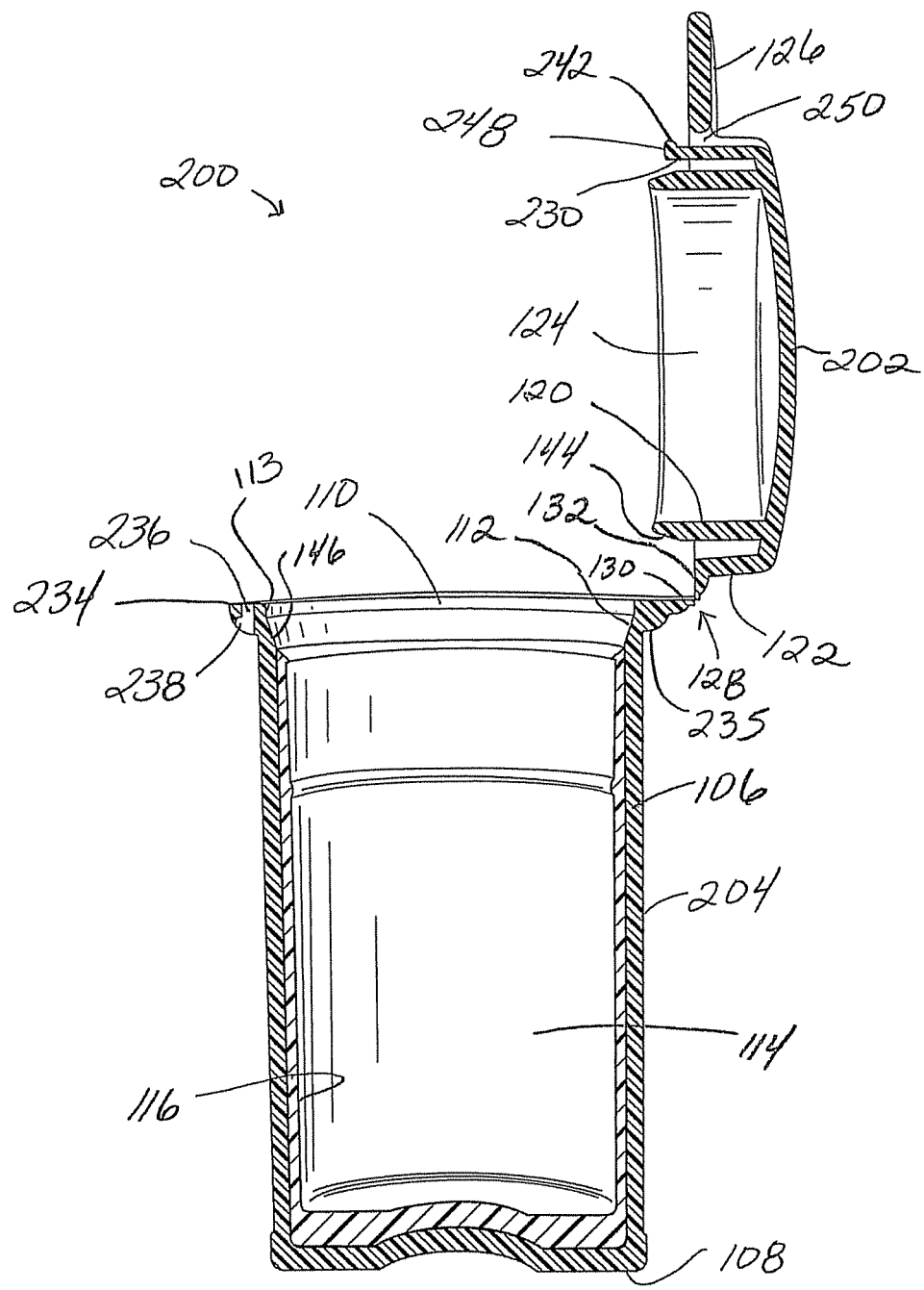
FIG. 10 is a cross sectional view of the container illustrated in FIG. 9 with the lid in an open position.
Figure 13:
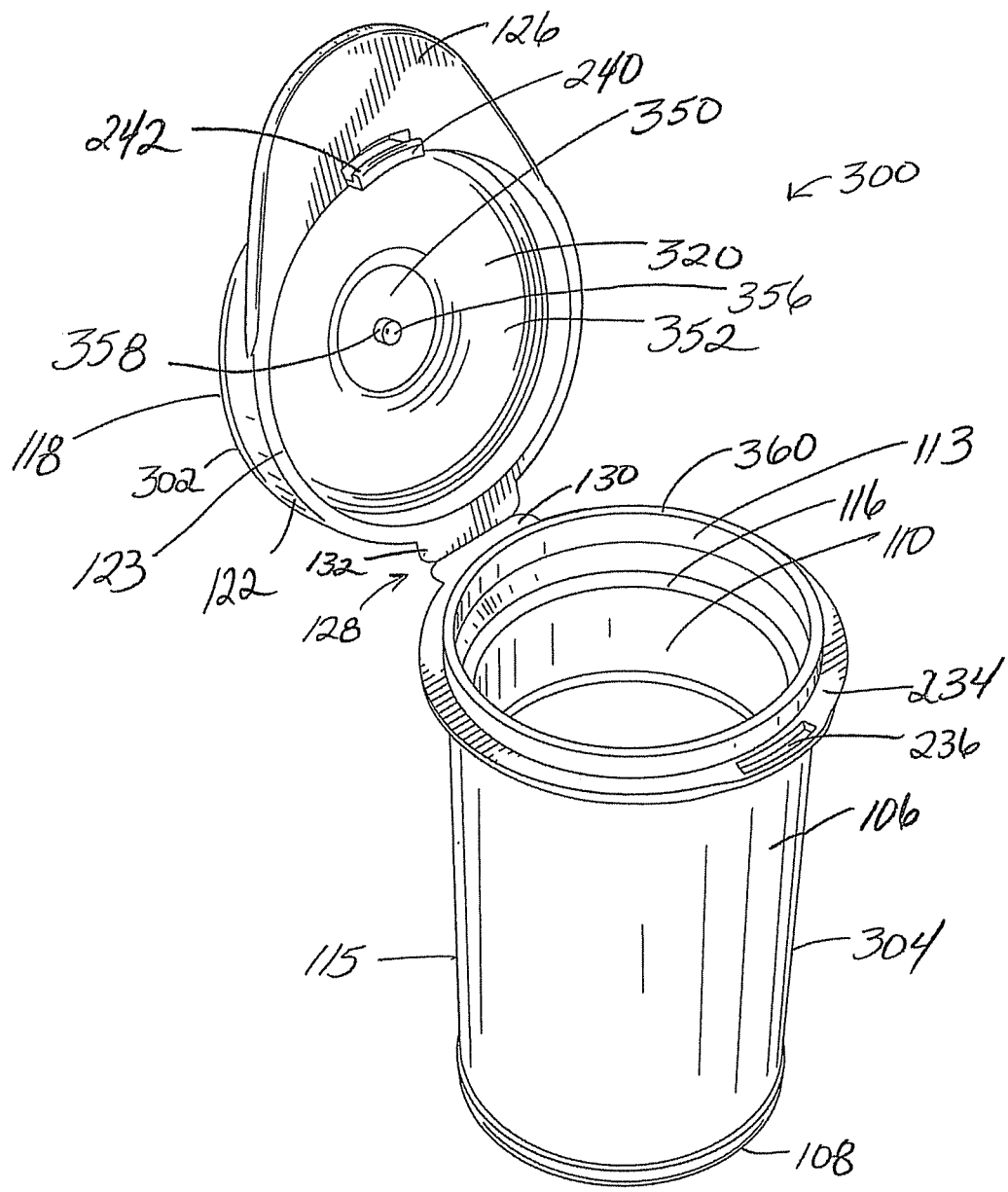
FIG. 13 is a perspective view of an embodiment of a container, shown with a lid in an opened position.

As shown in FIG. 1, the body 104 may have a generally tubular or cylindrical configuration, with a round cross section. However, as illustrated by FIGS. 3 and 4, the body 104' may have a variety of other cross-sectional configurations, including, for example, a non-round cross-sectional shape, such as rectangular, square, polygonal, or oval, among others. Further, the lid 102' may have a cross sectional configuration that mates that of the body 104, and which allows for a seal between the lid 102' and body 104', and more specifically, allows for the sealing of the interior space 114' of the body 104' when the lid 102' is in a closed position.

The lid 102 comprises a cap 118 and a seal 120. The lid 102 is configured to close the opening 110 of the body 102 when the lid 102 is seated on the body 104 in a closed position. The seal 120 may extend from the cap 118 and beyond the seating surface 123 of the lid 102 so that when the lid 102 is seated on the body 104, at least a portion of the seal 120 extends into the interior space 114 of the body 104. The lid 102 may also include a tab 126, such as a thumb tab, that may be pressed or pulled to assist with moving the lid 102 from a closed or opened position, and vice versa.

According to an embodiment of the present invention, at least a portion of the seal 120 is an inner ring. According to such an embodiment, the inner wall of the seal 120 may define an upper interior region 124. Therefore, when the lid 102 is in a closed position, the upper interior region 124 may be adjacent to the opening 110 of the body 104 and may provide additional space for products that extend beyond the interior space 114. Thus, according to an embodiment of the present invention, when the lid 102 is in a closed position, the container 100 may sealably house items or products generally between the base 108 of the body and the cap 118 of the lid 102.

The lid 102 may also include a skirt 122 that extends away from the cap 118. As shown in FIG. 2, at least a portion of the skirt 122 may have a generally tubular configuration, among others. The skirt 122 may surround at least a portion of the seal 120. Additionally, the skirt 122 may be offset from the seal 120 so that a gap is present between at least a portion of the inner walls of the skirt 122 and the outer walls of the seal 120.

According to an embodiment of the present invention, the lid 102 and body 104 are separate, individual components that are not integrally molded together. For example, the lid 102 and body 104 may be separately injection molded from thermoplastic material, such as, for example, a polypropylene, such as a moisture blocking polymeric material. Additionally, an active agent, such as a desiccating agent, and channeling agent may be blended into the polymer. Examples of such active materials are disclosed in one or more of U.S. Pat. Nos. 6,130,263, 6,080,350, 6,221,446, 6,124,006, 6,214,255, 6,194,079, 6,316,520, 6,465,532, 5,911,937, 6,174,952, 6,177,183, 6,486,231, 6,696,002, 6,460,271, 6,613,405, 6,852,783, RE40,941, and 7,005,459, which are incorporated herein by reference as if fully set forth.

Additionally, according to embodiments of the present invention in which the body 104 and/or lid 102 contain a desiccant material 116, the desiccant material 116 may be separately injection molded and assembled or formed in two shots in one injection mold.

According to an embodiment of the present invention, the lid 102 and body 104 are attached together by a hinge 128. The hinge 128 may be formed by a variety of mechanisms, including, for example, a mechanical fastener such as a pin, bolt, or screw, a plastic weld, or an adhesive, among others. In embodiments where the body 104 and lid 102 are integral, such as where these components are molded together or where they are molded separately and subsequently joined in an integral manner, by for example, plastic welding, the hinge 128 may be formed by an area joining the two where the material is thin enough to permit bending. The hinge 128 may allow the lid 102 to be pivotably moved from a closed position, as shown in FIG. 1, to an open position, as shown in FIG. 2, and vice versa. Further, the hinge 128 may be formed by joining a first extension 130 from the body 104 with a second extension 132 from the lid 102. For example, as shown in FIG. 2, the body 104 may include a rim 134 about the opening 110 of the body 104 from which the first extension 130 extends, while the second extension 132 may extend from the from the skirt 124 of the lid 102.

FIGS. 5-7 illustrate cross sectional views of the container 100 illustrated in FIG. 1. The seal 120 is configured to assist in creating a seal between the lid 102 and the body 104 when the lid 102 is seated on the body 104. Moreover, when the lid 102 is in a closed position, at least a portion of the seal 120 extends into the interior space 114 and abuts against at least a portion of the body sealing surface 112 on the inner surface 113 of the sidewall 106. The size and configuration of the seal 120 and the body sealing surface 112 may create a compressive force or a tension force between the seal 120 and the body sealing surface 112 that creates a seal or plug that controls the ingress and/or egress of moisture into the interior space 114 and isolates the interior space 114 from ambient conditions.

For example, according to an embodiment of the present invention, at least a portion of the body sealing surface 112 may have an inner diameter that is smaller than the outer diameter of at least a portion of the mating surface of the seal 120 of the lid 102. Such differences in diameters may result in pressure being asserted by the sealing surface 112 against the mating surfaces of the seal 120, and/or vice versa, that may create a seal between those abutting surfaces. Moreover, depending on the material used to construct the seal 120 and its size and configuration, such differences in diameters may result in at least a portion of the seal 120 being bent, deflected, compressed, and/or deformed by the pressures asserted thereon by the abutting engagement with the body sealing surface 112, which may cause the formation of a seal between the abutting surfaces of the seal 120 and the body sealing surface 112.

As shown in FIGS. 5-7, at least a portion of the seal 120 may include a tapered surface 144. Such a tapered surface 144 may assist with positioning the seal 120 inside the interior space 114 and against a portion of the body sealing surface 112 as the lid 102 is moved to a closed position. More specifically, the tapered surface 144 of the seal 120 may have a smaller diameter(s) than the inner diameter at the mouth of the opening 110 of the body 104 that allows the tapered surface 144 to initially enter into the interior space 114 with minimal or no interference from the sidewall 106, and specifically from the body sealing surface 112 so that the seal 120 may be properly positioned in the interior space 114. Such differences in the diameters at the tapered surface 144 of the seal 120 and the body sealing surface 112 at the mouth of opening 110, as well as the ability of the seal 120 to deflect, bend, or deform, may allow for leeway in the degree of accuracy required in the alignment and/or positioning of the lid 102 relative to the body 104 for the lid 102 to properly be closed and form a seal with the body 104.

Additionally, as shown in FIGS. 5-7, the at least a portion of the body sealing surface 112 may also include a tapered or chamfered surface 146 that mates with, and abuts against, the tapered surface 144 of the seal 120 when the lid 102 is in a closed position. The angle of the chamfer surface 146 may be selected to mate the angle or degree of taper of the tapered surface 144. Like the abutment of other portions of the body sealing surface 112 and seal 120, the diameters of these mating tapered and chamfer surfaces 144, 146 may be configured to assist in creating a sealable engagement between the lid 102 and body 104 that prevents the ingress and/or egress of moisture into/out of an interior space 114 of the container 100 and may be used to control the conditions in the interior space 114.

The container 100 may also include an attachment mechanism 148 that may assist in retaining or locking the lid 102 seated on the body 104 in a closed position. Further, the locking of the attachment mechanism 148 may maintain the seal 120 and body sealing surface 112 in compressive and/or tension engagement when the lid 102 is closed, and thereby maintain or lock the seal between the lid 102 and body 104. According to an embodiment of the invention, the subsequent unlocking of the attachment mechanism 148 and movement of the lid 102 from being seated in the body 104 to an opened position may break the seal between the lid 102 and body 104, and particularly the seal between the seal 120 and body sealing surface 112, which may result in an audible "popping" sound.

According to an embodiment of the present invention, the attachment mechanism 148 may include a claw 140 having a protrusion 142 that lockingly engages the lid 102. As shown in FIGS. 2 and 5-7, the lid 102 may include an aperture 136 and recess 138 that house or mate with at least a portion of the claw 140 and/or protrusion 142 when the lid is in a closed position. At least a portion of the aperture 136 and recess 138 may be located in the skirt 122 and/or tab 126 of the lid 102, or any combination thereof. The aperture 136 is sized to receive the insertion of at least a portion of a claw 140 that may extend away from the body 104, such as extending away from the rim 134. As shown in FIGS. 6 and 7, when the lid 102 is in a closed position, at least a portion of the claw 140 may be located in the gap between the inner wall of the skirt 122 and the outer wall of the seal 120. The positioning of the protrusion 142 in the recess 138 may create an interference and/or frictional engagement between the protrusion 142 and the lid 102 that maintains or locks the lid 102 in a closed position seated on the body 104, and thereby maintain a seal about the interior space 114. Furthermore, rather than engaging the lid 102 through a recess 138, a through hole may be formed in the lid 102 for passage of the claw 140, such that the protrusion 142 engages an outer surface of the lid 102, such as, for example, an upper surface 127 of the tab 126. Additionally, the tab 126 may assist with moving the lid 102 to/from a closed position so that the protrusion 142 engages/disengages with the recess 138.

The claw 140 may be configured to be resilient so that the claw 140 may bend or deflect when the protrusion 142 is pressed against the lid 102 as the lid 102 is being moved to or from a closed position. For example, as the lid 102 is being moved to a closed position and the claw 140 enters the aperture 136, the protrusion 142 may come into sliding contact with a surface of the lid 102 as the recess 138 is being moved closer to the protrusion 142. Such contact may cause the claw 140 to bend or deflect in a generally inward direction. When the protrusion 142 is able to engage with the recess 138, the claw 140 may return to an un-deflected or bent position, or have a reduced degree of deflection or bending. The resiliency of the claw 140 may be provided by the material used to construct the claw 140 and/or the size and configuration of the claw 140.

The claw 140 may be an integral part of the body 104, or may be a separate component that is operably attached to the flange 104. For example, according to one embodiment, the body 140 may be molded to include the claw 140. Alternatively, the claw 140 may be a separate component that may slide in an opening in the rim 134 of the body 104. According to such an embodiment, in addition to having a protrusion 142 at the upper end of the claw 140, the bottom end of the claw 140 may be configured so as to prevent the claw 140 from being disengaged from the body 104. In use, when the lid 102 is in a closed position, the bottom end of such a claw 140 may be moved toward the lid 102 until the protrusion 142 engages the recess 138.

FIGS. 8-12 illustrate a container 200 according an embodiment of the present invention having a lid 202, a body 204, and an attachment mechanism 248 that is configured to retain the lid 202 in a closed position. The attachment mechanism 248 may include a claw 240 having a protrusion 242. At least a portion of the attachment mechanism 240 may be housed in, or mate with, the body 204 when the lid 202 is in a closed position. For example, the body 204 may include an aperture 236 having a recess 238 through which the protrusion 242 may engage the body 204. More specifically, as shown in FIGS. 8-12, the claw 248 may be an integral part of the lid 204 that generally extends from the lid 202. Thus, when the lid 202 is in a closed position at least a portion of the claw 240 is positioned in an aperture 236 in the rim 234 or sidewall 106 of the body 204. For example, the claw 248 may extend from the cap 118 of the lid 202, be an extension of the skirt 122, be a protrusion from a side surface of the skirt 118, or protrude from a bottom surface of the tab 126, among other configurations. As shown in FIGS. 11 and 12, with the lid 202 in the closed position, the claw 240 may extend from the cap 118 or skirt 122, through an orifice 250 in the tab 126, and into the aperture 236 in the rim 234, where the protrusion 242 may engage the recess 238. Furthermore, rather than engage the body 204 through the recess 238, the protrusion 242 may engage an outer surface of the body 204, such as, for example, a lower surface 235 about the base of the rim 234, among others.

FIGS. 13-16 illustrate a container 300 having a lid 302, a body 304, and a seal 320. The seal 320 may include a seal base 350 and a sealing surface 352. The seal base 350 may include an orifice 354 that engages with a pin 356 that extends from the lid 302 to secure the seal 350 to the lid 302. The pin 356 may include a shoulder 358 having a diameter larger than the orifice 354 that assists in retaining the seal 350 in connection with the lid 302. The larger diameter of the shoulder 358 may create an interference that prevents the seal 320 from inadvertently becoming disengaged from the pin 356. The elastomeric nature of the seal 320 may allow the passage of the larger shoulder 358 through at least a portion of the orifice 354 when the seal 320 is being attached to the lid 302. The seal 320 and lid 302 may also be connected in a variety of other manners, including, for example, through the use of an adhesive, among others. For example, the seal 320 may include at least one mount that extends from the top of the seal 320 and engages at least one cavity in the lid 302. Like the seal 320, such a mount may be constructed from an elastomeric material and include a shoulder that may be deformed to fit into, and be retained by, the cavity of the lid 302.

The sealing surface 352 may extend from the seal base 350 and be configured so that at least a portion of the sealing surface 352 contacts at least a portion of the body 304 when the lid 302 is in a closed position so as to form a seal between the lid 302 and the body 304. As shown in FIGS. 14-16, according to an embodiment of the present invention, at least a portion of the sealing surface 352 may descend both outwardly and away from the seal base 350. Such a configuration may allow at least a portion of the sealing surface 352 to be in contact with the body 304 when the lid 302 is in a closed position and be subject to a compression force that may result in the deflection, deformation, or compression of at least a portion of the sealing surface 352. Further, such a configuration may provide space between the sealing surface member 352 and the lid 118 for at least a portion of the sealing surface 352 to be moved into when the seal 320 goes from a relaxed state when the lid is in an open position, to a compressed state when the lid 302 is in a closed position.

As shown in FIGS. 15 and 16, when the lid 302 is in a closed position, at least a portion of the sealing surface 352 is in contact with a lip 360 at the top of the sidewall 106 at the mouth of the opening 110 of the body 304. As shown in FIGS. 15 and 16, according to an embodiment, when the lid 302 is closed, the sealing surface 352 may engage at least a portion of a sidewall 106 of the body 304 that extends beyond the rim 134 to form a seal between the lid 302 and body 304. Extending the sidewall 106 beyond the rim 134 may result in, when the lid 302 is closed, the sidewall 106 providing interference that may cause at least a portion of the sealing surface 352 to be deflected, deformed, bent, or compress, which may assist in creating a seal between the lid 302 and the body 304. Additionally, the extended sidewall 106 may result in the formation of an additional seal between the sidewall 106 and inner surface of the skirt 122.

Further, the sealing surface 352 may be biased toward the body 304, such as toward the lip 360 and/or sidewall 106 when the lid 302 which may also assist in creating a seal between the lid 302 and the body 304 when the lid 302 is in a closed position. Additionally, the container 300 may also include an attachment mechanism 148, 248 to maintain or lock the lid 302 in a closed position so as to maintain the seal between the lid 302 and the body 304.

The seal 320 may have a variety of different configurations. Further, the outer perimeter of the seal 320 may be configured to conform to the shape of the lid 302, cap, 122, and/or skirt 122. For example, according to an embodiment of the present invention, the seal 320 may have a generally circular cross-sectional shape. However, the seal 320 may have a variety of other non-circular configurations, including for example, being square, rectangular, triangular, polygonal, or oval, among others.

Figure 17:
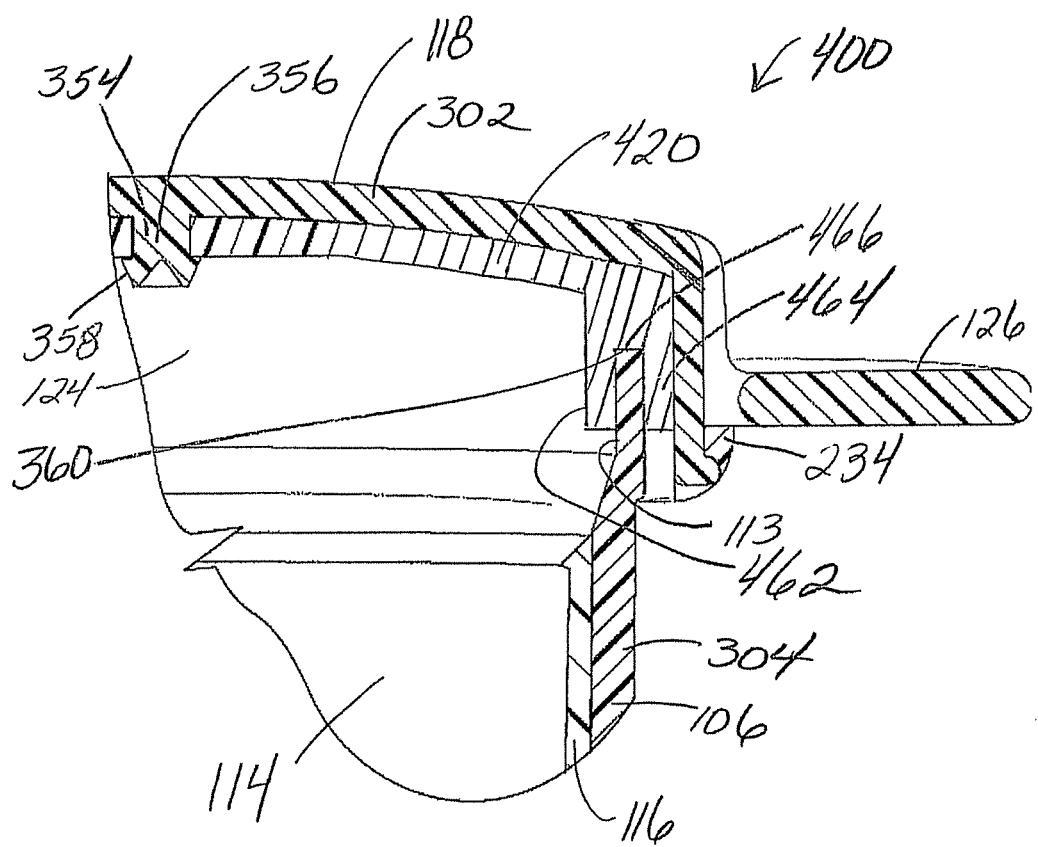
FIG. 17 is a cross sectional view of a portion of a container having a seal and a lid in the closed position.

While FIGS. 15 and 16 illustrate the outer portions of the sealing surface 352 in contact with the lip 360 when the lid 302 is in a closed position, the seal 320 may have other configurations that engage the lip 360 and/or other portions of the body 304. For example, as shown in FIG. 17, the container 400 may include a seal 420 having a first sealing surface 462 and/or a second sealing surface 464. According to such an embodiment, the first sealing surface 462 may be an inner sealing ring that is configured for engagement with at least a portion of the inner surface 113 of the sidewall 106. Additionally, the second sealing surface 464 may be an outer sealing ring that is configured to engage a portion of the outer surface 115 of the side wall 106. Further, between the first and second seals 462, 464 may be a sealing region 466 that engages the lip 360 of the body 304 when the lid 302 is in a closed position.

What is claimed is:

1. A resealable container comprising:
a body having a sidewall, a base, and an opening, the base and the opening being disposed at opposite ends of the body, the sidewall having an inner surface and an outer surface and defining an interior space in the body, the interior space being disposed between the opening and the base;
a lid pivotably joined to the body by a hinge to allow the lid to be moved between a closed position, in which the lid is seated on the body and an open position, in which access to the opening is provided, the hinge comprising a single axis of rotation about which the lid is pivotable relative to the body, the lid including a seating surface that contacts an upper end of the sidewall of the body when the lid is in the closed position, the lid including a seal extending downwardly beyond the seating surface such that when the lid is in the closed position, the seal extends into the interior space of the body and an outer wider surface of the seal, which is perpendicular to a plane of the seating surface, abuts against a body sealing surface of the inner surface of the sidewall to create a compressive force between the outer wider surface of the seal and the body sealing surface, thereby creating a plug between the lid and the body to control ingress of moisture into the interior space, the plug being positioned below the seating surface and the axis of rotation of the hinge, the seal having a bottom portion that includes a tapered outer surface that tapers radially inward from the outer wider surface of the seal above the tapered surface to facilitate movement of the lid from the open position to the closed position, such that when the lid is transitioned from the open position to the closed position, the tapered outer surface initially enters into the interior space with no interference from the body sealing surface or less interference with the body sealing surface than the outer wider surface of the seal has with the body sealing surface when the lid is in the closed position, the lid including a thumb tab that extends outwardly beyond the sidewall of the body when the lid is in the closed position, the thumb tab being configured to be pressed or pulled to assist with moving the lid from the closed position to the opened position, the lid further including an extension positioned radially outward relative to the seal, the extension depending downwardly from a front portion of the lid when the lid is in the closed position, the extension and seal defining an aperture therebetween, the extension comprising a through hole facing the aperture, the through hole defining a floor surface and a ceiling surface within the extension; and
an attachment mechanism configured to retain the lid to the body in the closed position, the attachment mechanism including a protrusion extending from the outer surface of the sidewall, the protrusion being configured to extend into and thereby lockingly engage with the through hole of the extension such that the protrusion is positioned between the floor surface and ceiling surface to assist in retaining the lid in the closed position, the protrusion being configured to disengage from the through hole of the extension in response to application of sufficient upward pressure to the thumb tab so as to unlock the attachment mechanism, thereby allowing the lid to be movable from the closed position to the open position by pressing up or pulling up on the thumb tab, wherein the attachment mechanism is located solely on an opposite side of the body from the hinge.

2. The resealable container of claim 1, wherein the attachment mechanism comprises only one single protrusion configured to lockingly engage the through hole of the lid.

3. The resealable container of claim 1, wherein movement of the lid from the closed position to the open position creates an audible popping sound.

4. The resealable container of claim 1, further comprising:
a desiccant material disposed within the interior space of the body, wherein the desiccant material is a liner or sleeve attached to an interior of the sidewall of the body.

5. The resealable container of claim 1, wherein the protrusion extends from a claw.

6. The resealable container of claim 5, wherein the claw extends upwards above the opening.

7. A resealable container comprising:
a body having a sidewall, a base, and an opening, the base and the opening being disposed at opposite ends of the body, the sidewall having an inner surface and an outer surface and defining an interior space in the body, the interior space being disposed between the opening and the base;
a lid pivotably joined to the body by a hinge to allow the lid to be moved between an open position and a closed position, the hinge comprising a single axis of rotation about which the lid is pivotable relative to the body, the lid including a cap and a thumb tab that extends outwardly from the lid beyond the sidewall of the body when the lid is in the closed position, the thumb tab being configured to be pressed or pulled to assist with moving the lid from the closed position to the opened position and back, the lid further including an aperture and an extension depending downwardly from a front portion of the lid when the lid is in the closed position, the extension having a through hole facing the aperture, the through hole defining a floor surface and a ceiling surface within the extension, the lid being configured to be seated on the body when the lid is in the closed position and to allow access to the interior space when the lid is in the open position, the lid including a seating surface that contacts an upper end of the sidewall of the body when the lid is in the closed position, the lid including a seal extending downwardly beyond the seating surface such that when the lid is in the closed position, the seal extends into the interior space of the body and an outer wider surface of the seal, which is perpendicular to a plane of the seating surface, abuts against a body sealing surface of the inner surface of the sidewall to create a compressive force between the outer wider surface of the seal and the body sealing surface, thereby creating a plug between the lid and the body to control ingress of moisture into the interior space, the plug being positioned below the seating surface and the axis of rotation of the hinge, the seal having a bottom portion that includes a tapered outer surface that tapers radially inward from the outer wider surface of the seal above the tapered surface to facilitate movement of the lid from the open position to the closed position, such that when the lid is transitioned from the open position to the closed position, the tapered outer surface initially enters into the interior space with no interference from the body sealing surface or less interference with the body sealing surface than the outer wider surface of the seal has with the body sealing surface when the lid is in the closed position; and attachment means extending outwardly from the outer surface of the sidewall for securing the lid to the body in the closed position and facilitating maintenance of the plug between the body and the lid when the lid is seated on the body, the attachment means being configured to lockingly engage the through hole of the extension such that a portion of the attachment means is positioned between the floor surface and ceiling surface to assist in retaining the lid in the closed position, the attachment means being configured to disengage from the through hole and thus unlock in response to application of sufficient upward pressure to the thumb tab, thereby allowing the lid to be movable from the closed position to the open position by pressing up or pulling up on the thumb tab, wherein the attachment means is located solely on an opposite side of the body from the hinge.

8. The resealable container of claim 7, wherein the attachment means includes a protrusion on the body, the protrusion being configured to lockingly engage the through hole to assist in retaining the lid seated on the body in the closed position.

9. The resealable container of claim 7, further comprising:
a desiccant material disposed within the interior space of the body, wherein the desiccant material is a liner or sleeve attached to an interior of the sidewall of the body.

10. The resealable container of claim 7, wherein the aperture is positioned between the through hole and the seal.

11. A resealable container comprising:
a body having a sidewall, a base, and an opening, the base and the opening being disposed at opposite ends of the body, the sidewall having an inner surface and an outer surface and defining an interior space in the body, the interior space being disposed between the opening and the base;
a lid pivotably joined to the body by a hinge to allow the lid to be moved between an open position and a closed position, the hinge comprising a single axis of rotation about which the lid is pivotable relative to the body, the lid including a cap and a thumb tab that extends outwardly from the lid beyond the sidewall of the body when the lid is in the closed position, the thumb tab being configured to be pressed or pulled to assist with moving the lid from the closed position to the opened position and back, the lid further including an aperture and a through hole facing the aperture, the through hole defining a floor surface and a ceiling surface within the lid the lid being configured to be seated on the body when the lid is in the closed position and to allow access to the interior space when the lid is in the open position, the lid including a seating surface that contacts an upper end of the sidewall of the body when the lid is in the closed position, the lid including a seal extending beyond the seating surface such that when the lid is seated on the body, the seal extends into the interior space of the body and an outer wider surface of the seal, which is perpendicular to a plane of the seating surface, abuts against a body sealing surface of the inner surface of the sidewall at a position below the seating surface and the axis of rotation of the hinge to create a compressive force between the outer wider surface of the seal and the body sealing surface, the seal having a bottom portion that includes a tapered outer surface that tapers radially inward from the outer wider surface of the seal above the tapered surface to facilitate movement of the lid from the open position to the closed position, such that when the lid is transitioned from the open position to the closed position, the tapered outer surface initially enters into the interior space with no interference from the body sealing surface or less interference with the body sealing surface than the outer wider surface of the seal has with the body sealing surface when the lid is in the closed position; and an attachment mechanism for securing the lid to the body in the closed position and facilitating maintenance of a sealing relationship formed by the compressive force between the outer wider surface of the seal and the body sealing surface when the lid is seated on the body, the attachment mechanism including a claw on the outer surface of the sidewall, the claw being configured to protrude into the aperture and extend into the through hole so as to lockingly engage with the through hole such that a portion of the claw is positioned between the floor surface and ceiling surface to assist in retaining the lid seated on the body in the closed position, the claw being configured to disengage from the through hole in response to application of sufficient upward pressure to the thumb tab so as to unlock the attachment mechanism, thereby allowing the lid to be movable from the closed position to the open position by pressing up or pulling up on the thumb tab, wherein the attachment mechanism is located solely on an opposite side of the body from the hinge.

12. The resealable container of claim 11, wherein the claw is located on the body, the claw including a protrusion being configured to lockingly engage the through hole of the lid to assist in retaining the lid seated on the body in the closed position.

13. The resealable container of claim 12, wherein at least a portion of the protrusion extends into the through hole when the lid is in the closed position.

14. The resealable container of claim 11, further comprising:
a desiccant material disposed within the interior space of the body, wherein the desiccant material is a liner or sleeve attached to an interior of the sidewall of the body.

15. The resealable container of claim 11, wherein the aperture is positioned between the through hole and the seal.

16. The resealable container of claim 1, wherein the protrusion is spaced radially outwardly from the seal when the lid is in the closed position.

17. The resealable container of claim 7, wherein the attachment means is spaced radially outwardly from the seal when the lid is in the closed position.

18. The resealable container of claim 11, wherein the claw is spaced radially outwardly from the seal when the lid is in the closed position.

* * * * *